US007824340B2

(12) United States Patent
Lee et al.

(10) Patent No.: US 7,824,340 B2
(45) Date of Patent: Nov. 2, 2010

(54) PULSIMETER SENSOR USING MAGNETIC THIN FILMS

(75) Inventors: Sang Suk Lee, Gangwon-Do (KR); Do Guwn Hwang, Gangwon-Do (KR); Ki Wang Kim, Seoul (KR); Sun Wook Kim, Gangwon-Do (KR); Hyeon Ho Kim, Seoul (KR)

(73) Assignee: Sangji University Industry Academy Cooperation Foundation (KR)

( * ) Notice: Subject to any disclaimer, the term of this patent is extended or adjusted under 35 U.S.C. 154(b) by 966 days.

(21) Appl. No.: 11/583,580

(22) Filed: Oct. 19, 2006

(65) Prior Publication Data

US 2007/0118040 A1 May 24, 2007

(30) Foreign Application Priority Data

Oct. 19, 2005 (KR) ...................... 10-2005-0098677

(51) Int. Cl.
*A61B 5/02* (2006.01)
(52) U.S. Cl. ....................... 600/500; 600/501; 600/502; 600/503; 600/504
(58) Field of Classification Search ..................... 600/9, 600/13, 15, 500–504; 73/1.37, 1.41, 570, 73/584–588, 779, 862.333, 862, 861.08, 73/861.11–861.12, 541.16, 514, 31
See application file for complete search history.

(56) References Cited

U.S. PATENT DOCUMENTS

| 4,709,209 | A | * | 11/1987 | Murakami et al. | ........ 178/18.07 |
| 4,860,761 | A | * | 8/1989 | Yamasawa et al. | .......... 600/499 |
| 4,972,841 | A | * | 11/1990 | Iguchi | .......... 600/528 |
| 5,206,590 | A | | 4/1993 | Dieny et al. | |
| 5,650,958 | A | | 7/1997 | Gallagher et al. | |
| 5,828,525 | A | * | 10/1998 | Iwasaki et al. | .............. 360/314 |
| 6,126,589 | A | * | 10/2000 | Brooks | ........................ 600/15 |
| 6,338,899 | B1 | * | 1/2002 | Fukuzawa et al. | ...... 360/324.12 |
| 6,722,206 | B2 | * | 4/2004 | Takada | ........................ 73/779 |
| 6,944,049 | B2 | * | 9/2005 | Hoenigschmid et al. | .... 365/158 |
| 2004/0238796 | A1 | * | 12/2004 | Abe | .......................... 252/500 |

FOREIGN PATENT DOCUMENTS

| JP | 2000157503 | 6/2000 |
| KR | 10-2001-0028668 | 4/2001 |

(Continued)

OTHER PUBLICATIONS

Magnetostriction and Magnetostrictive Materials—http://aml.seas.ucla.edu/research/areas/magnetostrictive/mag-composites/Magnetostriction%20and%20Magnetostrictive%20Materials.htm.

*Primary Examiner*—Robert L Nasser
*Assistant Examiner*—Michael D'Angelo
(74) *Attorney, Agent, or Firm*—Gerald E. Hespos; Michael J. Porco

(57) ABSTRACT

The present invention relates to a noninvasive medical pulsimeter sensor using magnetic thin films. By forming a pulse-sensing part array with magnetic sensors such as GMR devices, MTJ devices and the likes, over the skin-contacting part which consists of a magnetic material, the present invention increases the integrity of sensors, minimizes the time for searching the pulse and it is applicable widely to portable pulsimeters and the likes.

16 Claims, 5 Drawing Sheets

FOREIGN PATENT DOCUMENTS

| | | |
|---|---|---|
| KR | 10-2002-0096224 | 12/2002 |
| KR | 1020020092557 | 12/2002 |
| KR | 1020030013808 | 2/2003 |
| KR | 10-2000-0065658 * | 7/2004 |
| KR | 20-2004-0012729 * | 8/2004 |
| KR | 20-0358195 | 8/2004 |

* cited by examiner

FIG. 2

| Pulse qualities (28) | strength | palpating location | | | width | | effective length | | period | | | slowness of up and down | |
|---|---|---|---|---|---|---|---|---|---|---|---|---|---|
| | | shallow | deep | very deep | wide | narrow | long | short | long | short | no beat period | slow | fast |
| floating pulse | | ○ | ○ | ○ | | | | | | | | | |
| deep pulse | | ⊙ | ○ | ○ | | | | | | | | | |
| slow pulse | | | | | | | | | ○ | | | | |
| rapid pulse | | | | | | | | | | ○ | | | |
| large pulse | | | | | ○ | | | | | | | | |
| short pulse | | | | | | ○ | | | | | | | |
| long pulse | | | | | | | ○ | | | | | | |
| short pulse with short extent | | | | | | | | ○ | | | | | |
| slippery pulse | | | | | | | | | | | | | ○ |
| uneven pulse | | | | | | | | | | | | | ○ |
| abrupt pulse | | | | | | | | | | ○ | ○ | | |
| knotted pulse | | | | | | | | | ○ | | ○ | | |
| regularly intermittent pulse | | | | | | | | | | | ○ | | |
| moderate pulse | | | | | | | | | | | | | |
| full pulse | ● | | | | ○ | | | | | | | | |
| faint pulse | • | | | | | ○ | | | | | | | |
| weak pulse | | ⊙ | • | • | | ○ | | | | | | | |
| solid pulse | ● | | | | | | | | | | | | |
| deficient pulse | • | | | | | | | | | | | | |
| tympanic pulse | | ● | • | • | | | | | | | | | |
| firm pulse | | ⊙ | ● | ● | | | | | | | | | |
| tremulous pulse | | | | | | | | | ○ | ○ | | ○ | |
| hidden pulse | | ⊙ | ⊙ | ○ | | | | | | | | | |
| scattered pulse | | ⊙ | ⊙ | ⊙ | | | | | | | | | |
| hollow pulse | | ○ | ⊙ | ⊙ | | | | | | | | | |
| soft pulse | | • | ⊙ | ⊙ | | | | ○ | | | | | |
| taut pulse | | | | | | | | | | | | | |
| tense pulse | ● | | | | | | | | | | | | | conventional pressure sensors can measure only these 7 qualities.

● strong  • weak  ⊙ absence  ○ presence

# PULSIMETER SENSOR USING MAGNETIC THIN FILMS

This application claims priority under 35 U.S.C. §119 of Korean Patent Application 2005-0098677, filed on Oct. 19, 2005, the entire contents of which are hereby incorporated by reference.

BACKGROUND OF THE INVENTION

1. Field of the Invention

The present invention relates to a pulsimeter sensor using magnetic thin films, and more particularly to a medical pulsimeter sensor, wherein a pulse-sensing part array consists of GMR (Giant Magneto Resistance) devices or MTJ (Magnetic Tunnel Junction) devices and the pulse-sensing part array is located over a skin-contacting part which consists of a magnetic material. When a radial pulse transferred to the magnetic material of the skin-contacting part results in changes in a magnetic field of the lower part of the pulse-sensing part array, and these changes in the magnetic field can be detected by the pulse-sensing part array. Finally, according to the present invention, the radial pulse can be measured noninvasively by detecting the changes of the magnetic field.

2. Description of the Related Art

Currently, most medical detecting sensors for the pulse are the invasive sensors, which detect the changes in the blood pressure by injecting tubes into the blood vessels, or the noninvasive sensors using pressure sensors.

Particularly, the pulsimeter sensor using pressure sensors has been researched many times due to its noninvasivity and the Korean Patent Publication Number 10-2001-0028665 regarding the medical pulsimeter sensor, the Korean Patent Publication Number 10-2002-96224 regarding the automatic pulsimeter, and the Korean Utility Registration Number 20-0358195 regarding the pulse wave measuring device et al. are some examples.

In the Korean Patent Publication Number 10-2001-28668, as shown in FIG. 1, the medical pulsimeter sensor includes a pressure-sensing sensor 4 including a silicon layer 1, which is adhered closely to the upper skin at the radial artery and close up the air layer tight to sense the pressure change of the air layer depending on the vibration of a pulse wave, a silicon gel 2, which transfers the pressure change of the air layer, and a pressure-measuring plate 3, which measures the pressure changes to be transferred by the silicon gel; a silicon gum 5, having a hole fit for the pressure-sensing part, wrapping the pressure-sensing part and being adhered to the front side of the pressure-sensing sensor 4 and making the pressure-sensing sensor 4 fixed to the skin of the examinee; and a fortified plastic plate 6, being adhered to the back side to the pressure-sensing sensor 4, and transferring the variable pressure from the back side of the pressure-sensing sensor 4 to the skin of the examinee.

The silicon layer 1 and the silicon gel 2, which are in front of the pressure-measuring plate 3, eliminate a cold feeling and unnecessary stimulus of metals, of which the conventional pulse-sensing part is comprised. However, the conventional pulsimeter sensor using pressure sensors has the problems that it unnecessarily closes up the air layer tight, transfers the pressure changes indirectly to a pressure-measuring plate and is unable to measure the exact pulse. And it is impossible to search for the location of the pulse depending on each person and measure an exact pulse quickly with the conventional pulsimeter sensor using pressure sensors.

By the way, Oriental medical doctors have diagnosed the three pulse locations on the wrist, over the radial artery classified as Chon, Gwan and Cheok. The "Gwan" is located on the coronal process of the radial artery on the wrist, the "Chon" is located on the spot 1~1.3 cm from the Gwan toward a palm of the hand, and the "Cheok" is located on the spot 1~1.3 cm from the Gwan toward an elbow. The doctor places the index, middle and ring fingers on the examinee's the Chon, Gwan and Cheok with three different degrees of pressing, that is, moderate (the "Bu" state), hard (the "Jung" state), and light (the "Chim" state).

To improve problems which the conventional pulsimeters have, the Korean Patent Publication Number 10-2002-96224 regarding the automatic pulsimeter, disclosed invention about mechanical embodiments of the way Oriental medical doctors feel the pulse with one pressure sensor and the Korean Utility Registration Number 20-0358195 regarding the pulse wave measuring device disclosed invention measuring the three regions of Chon, Gwan, and Cheok simultaneously with three pressure sensors.

However, the conventional arts use pressure sensors such as a piezoelectric device, and have the following problems:

First, it is possible to understand the time characteristics to some extent by measuring the changes in the pulse pressure (wave form) with the pressure sensors, but it is hard to understand the spatial characteristics (three-dimensional configurations) of the pulse such as the depth, the area, the length of the pulse and so on, which have been recognized more important in the traditional pulse diagnosis.

Accordingly, as shown in FIG. 2, only 7 qualities, those are related with the time characteristics, in words, slow pulse, rapid pulse, slippery pulse, uneven pulse, abrupt pulse, knotted pulse, and regularly intermittent pulse, can be understood by the conventional arts among 28 qualities that have been used in traditional pulse diagnosis. Therefore, there has been a limitation on replacing the traditional pulse diagnosis by examiners with these mechanical pulsimeters.

Second, products using the pressure sensors to understand the spatial characteristics of the pulse have been manufactured recently, but there is a limitation on the degree of integrity for pressure-sensors. Therefore, there is nothing but to get minimum spatial information about the pulse through an excess interpolation.

Third, to measure the spatial characteristics of the pulse properly, sensors should find out the location of the radial artery accurately. However, only several pressure sensors cannot search the center of the radial artery properly, and it takes too long to search the locations of the pulses.

Fourth, because of the nature of the pressure sensors of having a weakness in movement noises, it is impossible to measure pulses with wearing themselves, and this characteristic has an application limit to a portable apparatus.

Lastly, most pressure sensors have been equipped with measuring means of a rigid body, and an applying pressure on measurement of a pulse generates a pain.

SUMMARY OF THE INVENTION

To solve the problems which the conventional pulsimeter sensors have, the present invention is directed to a pulsimeter sensor using magnetic thin films.

To achieve the objectives of the present invention, a pulsimeter sensor is characterized by using magnetic thin films and including a skin-contacting part 10, formed with a magnetic material to be contacted to a skin to examine the pulse; a pulse-sensing part 20, located some distance from the skin-contacting part and formed as an array type of unit cells 22` with two magnetic films or more; and a spatial part 30, located between the skin-contacting part 10 and the pulse-sensing part 20, as shown in FIG. 3.

The present invention embodies a pulse-sensing part of an array type using a magnetic sensor as a minute unit cell. As a result, it is possible to minimize the time to search for the locations of the pulse and to measure the pulse which the conventional pressure sensors could not measure, and understand the spatial characteristics of the pulse completely. Therefore, it is possible to search for all 28 qualities of the traditional pulse diagnosis according to the present invention.

And, a GMR device or a MTJ device as a magnetic sensor can be diminished in size by a semiconductor lithography process, and it has little measuring fault according to the movements of the examinee, and it is possible to design various applications such as wrist watches, rings and IC chips as a wearable (portable) pulsimeter.

Furthermore, while the conventional pulsimeters using pressure sensors have a problem to generate a pain by applying a pressure into a skin, the present invention receives the pulse through a flexible magnetic material of a skin-contacting part, and it does not generate a pain.

BRIEF DESCRIPTION OF THE DRAWINGS

The invention may be better understood by the drawings that are briefly described below and attached hereto, in the several figures of which identical reference numbers (if any) refer to identical or similar elements.

FIG. 2 shows pulse characteristics seen in a traditional pulse diagnosis.

DETAILED DESCRIPTION OF THE PREFERRED EMBODIMENTS

A detailed description of preferred embodiments of the present invention is provided below with respect to the accompanying drawings.

In these drawings, the following reference numbers are used throughout: reference number 10 indicates a skin-contacting part, 20 means a pulse-sensing part, 22 means a unit cell, 30 means a spatial part, 222 and 228 mean an electric conducting layer, 224 means a variable ferromagnetic layer (a free layer), 225 means a nonmagnetic layer and 226 means a fixed ferromagnetic layer (a pinned layer).

A magnetic material of a skin-contacting part 10 of the present invention can be submicron magnetic nano-particles like magnetic nano-beads, of which their locations can be changed easily depending on the vibration of the pulse, or ultra thin magnetic films, comprised of small permanent magnets.

It is preferable that the magnetic nano-particles are Co, $Fe_3O_4$ or $Fe_2O_3$ and the ultra thin magnetic films are ribbon-type magnetic pads or small circular plate-type magnetic chips. In a case of using the ribbon-type magnetic pads for a magnetic material, plastic magnets of 200~300 Oe at a 3 mm distance are more preferable. The size of the ribbon-type magnetic pads is determined by the pulse-sensing part 20, and for example, the ribbon type magnetic pads can be shaped with 5 stripes, of which a stripe is 1.0 mm×12 mm. In this instance, there is an advantage that it is possible to fix the skin-contacting part 10 with grooves which were made by stripes of the magnetic pads.

Especially, it is preferable that the skin-contacting surface of the skin-contacting part 10 is made of soft materials not to press skin.

Next, a unit cell 22 of the pulse-sensing part 20 array can be a GMR device or a MTJ device, regardless of any structure it may have.

Many researches in these devices as memory devices for the next generation have already been investigating by semiconductor memory manufacturers (Refer to U.S. Pat. Nos. 5,206,590, 5,650,958 and so on.). Therefore, matters relevant to the present invention only are described here briefly.

Figure 1:
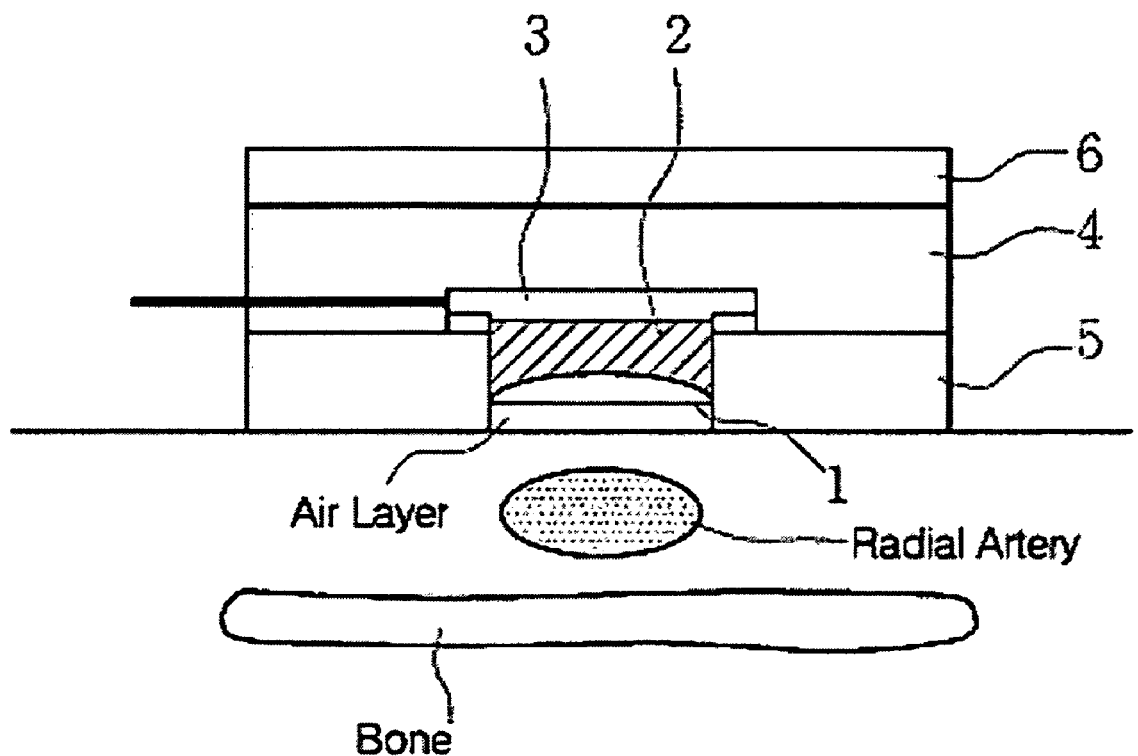
FIG. 1 is a cross-section of a conventional pulsimeter sensor.
Figure 3:
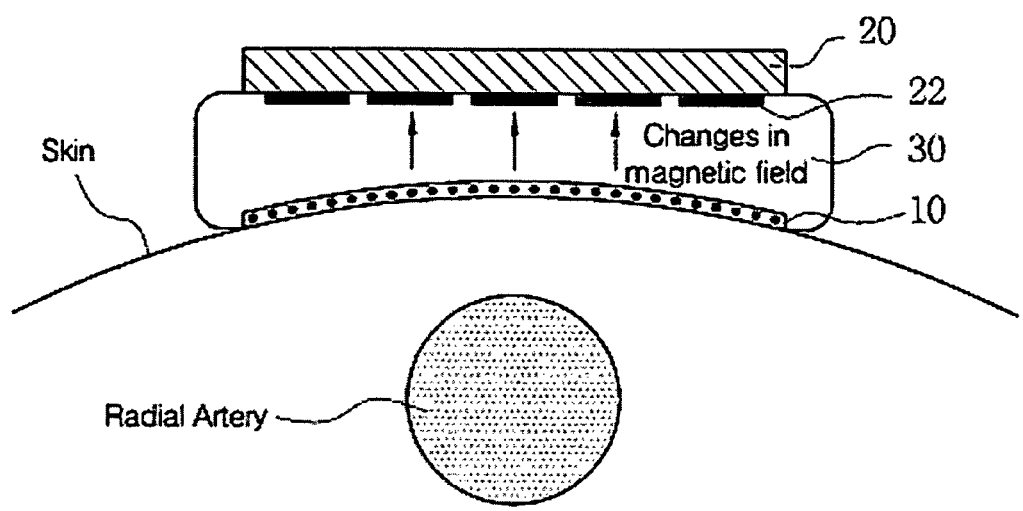
FIG. 3 is a cross-section of the pulsimeter sensor of the present invention.
Figure 4:
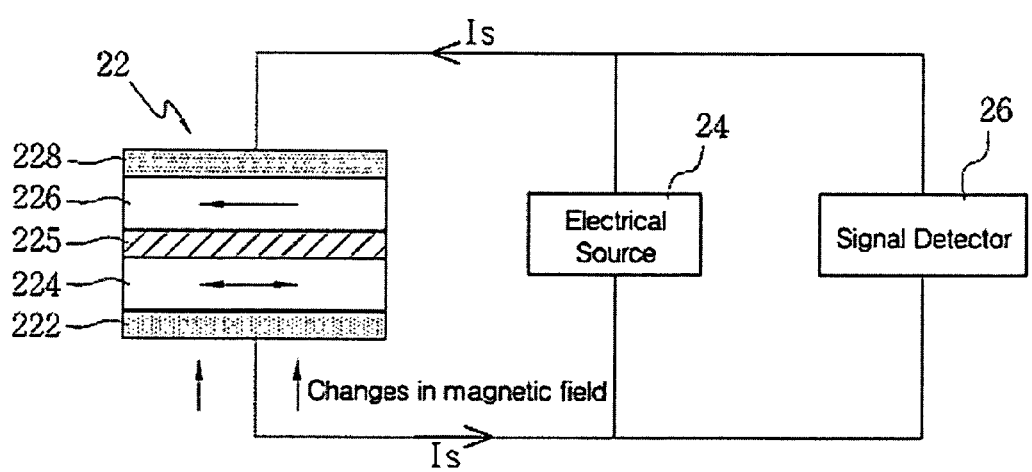
FIG. 4 shows an electrical connection to a unit cell of the present invention.

A GMR device, which is used as a unit cell 22 in the present invention, is usually called a SV sensor, showing Spin Valve effects. As shown in FIG. 4, a GMR device is made of one pinned layer 226, which is unidirectionally magnetized by an anti-ferromagnetic layer, and one free layer 224, of which magnetization can be turned freely by the external field, which the two ferromagnetic layers 224 and 226 are spaced by a nonmagnetic layer 225, and electric conducting layers 222 and 228 for supplying the longitudinal bias to each layer are deposited to the each one end 222 of the free layer 224 and the pinned layer 226, and an electrical source (a current source) 24 can be connected electrically to a signal detector 26 through the both conducting layers 222 and 228, and it can detect a resistance of the GMR device.

Figure 5:
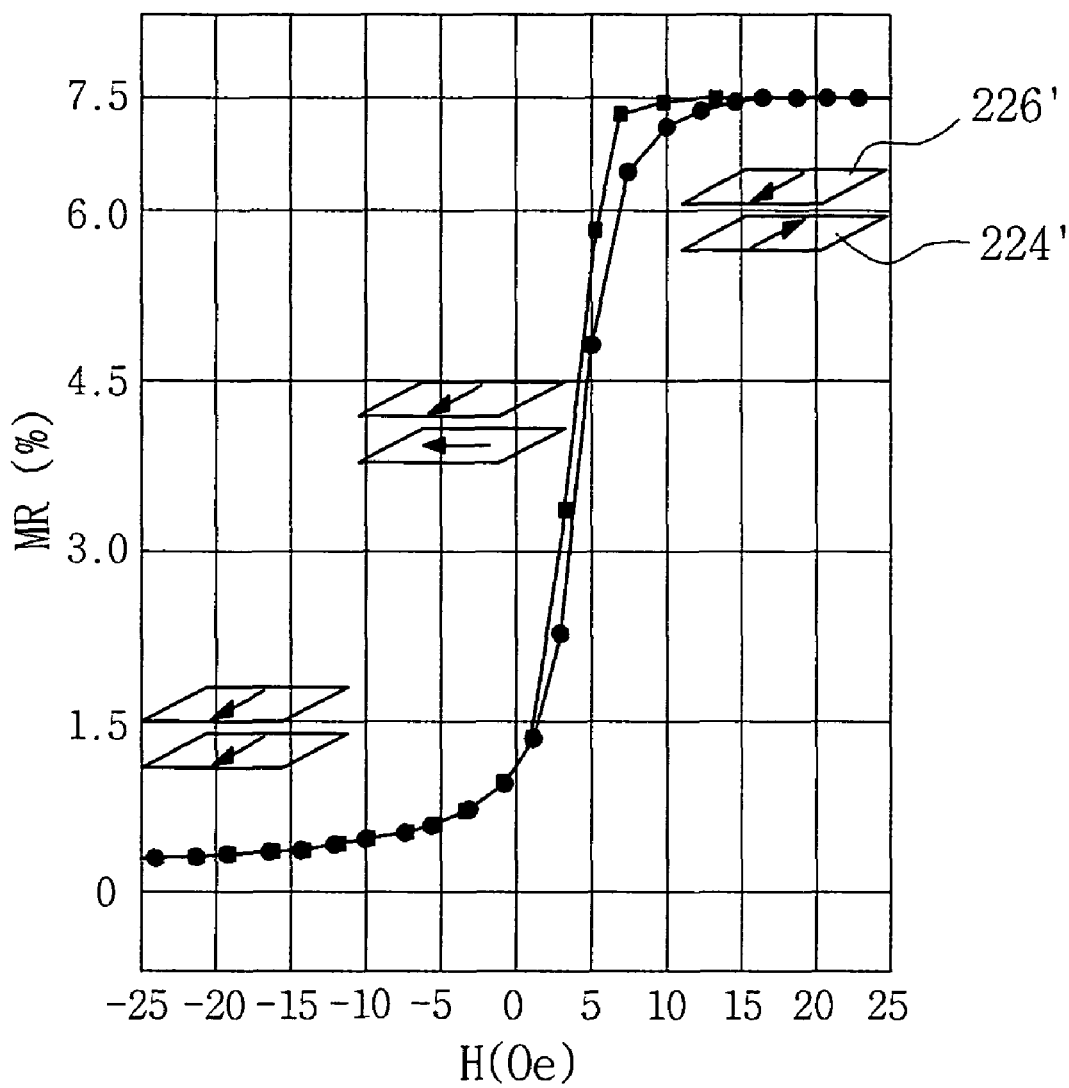
FIG. 5 shows an electrical operational characteristic of a unit cell for the external magnetic field.

As shown in FIG. 5, the GMR operates in a manner that when the magnetization 224' of the free layer is turned to be the same as the direction 226' of the pinned layer depending on the external magnetic field, a magnetic resistance (MR) gets smaller and when it is turned to be different from the direction 226' of the pinned layer, a magnetic resistance (MR) gets larger.

The present invention uses the operational characteristics of the GMR device. Therefore, when the magnetic material of the skin-contacting part 10 moves depending on the pulse of the radial artery, the magnetic material changes the magnetic field and this change in the magnetic field can be detected and responded by the free layer 224 of the GMR device. Then the response of the free layer 224 can be expressed at an external signal detector 26 as an electrical signal, such as a voltage, caused by changes in the magnetic resistance, and we can understand the pulsatory motion of the radial artery by analyzing the signals from the external signal detector 26 three-dimensionally.

The free layer 224 and/or the pinned layer 226 can be comprised of more than two thin films, which are different from each other. And the pinned layer 226 can include an anti-ferromagnetic layer, which can magnetize the pinned layer unidirectionally regardless of the magnetic field. A cap layer can be deposited further to the free layer 224 and/or the pinned layer 226 before the electric conducting layers 222 and 228 are deposited.

More specifically, it is preferable that the free layer 224 is formed of a CoFe layer and a NiFe layer orderly from one side of the nonmagnetic layer 225, and the pinned layer 226 is formed of a CoFe layer and a IrMn layer orderly from the one side of the nonmagnetic layer. It is also preferable that the nonmagnetic layer 225 is a Cu layer and the cap layer (not shown) is a Ta layer.

Furthermore, it is preferable that the CoFe layer of the free layer 224 is 1.8~2.2 nm (2.0 nm is more preferable), the NiFe layer is 3.8~4.2 nm (4.0 nm is more preferable), the CoFe layer of the pinned layer 226 is 3.3~3.7 nm (3.5 nm is more preferable), the IrMn layer is 13~17 nm (15.0 nm is more preferable), the Cu layer is 2.5~2.9 nm (2.7 nm is more preferable), and the Ta layer is 3~7 nm (5.0 nm is more preferable).

Regarding the free layer 224, the pinned layer 226, the nonmagnetic layer 225 and the cap layer (not shown), the materials and thickness of each layer is not limited to the said embodiments and any materials and thickness of each layer will be satisfied as long as the GMR device shows the operational characteristics by the magnetic material of the skin-contacting part 10.

In the meantime, a MTJ device, which is used as a unit cell 22 in the present invention, is comprised of two ferromagnetic layers spaced by an insulating tunnel barrier layer instead of a layer of nonmagnetic layer from the GMR device. The tunnel barrier layer should be enough thin to generate a quantum-mechanical tunneling of electron carriers between ferromagnetic layers. Because the tunneling is dependent on the magnetization of two ferromagnetic layers, one of ferromagnetic layers should be a pinned layer, of which magnetization is independent on the external electric field, and the other ferromagnetic layer should be a free layer, of which magnetization is dependent on the external electric field. And when the external electric field (signal) turns the magnetization of the free layer, the tunneling of the electron carriers for the insulating tunnel barrier layer is affected, and finally, the resistance of the MTJ device is changed. The changes in the resistance of the MTJ can be detected as signals like voltages.

Therefore, the MTJ device, either, can be a sensor for detecting changes in the magnetic field by the magnetic material of the skin-contacting part 10, which moves depending on the pulsatory motion of the radial artery. Any other magnetic sensors can be replaced within the technical thought of the present invention.

Figure 6:
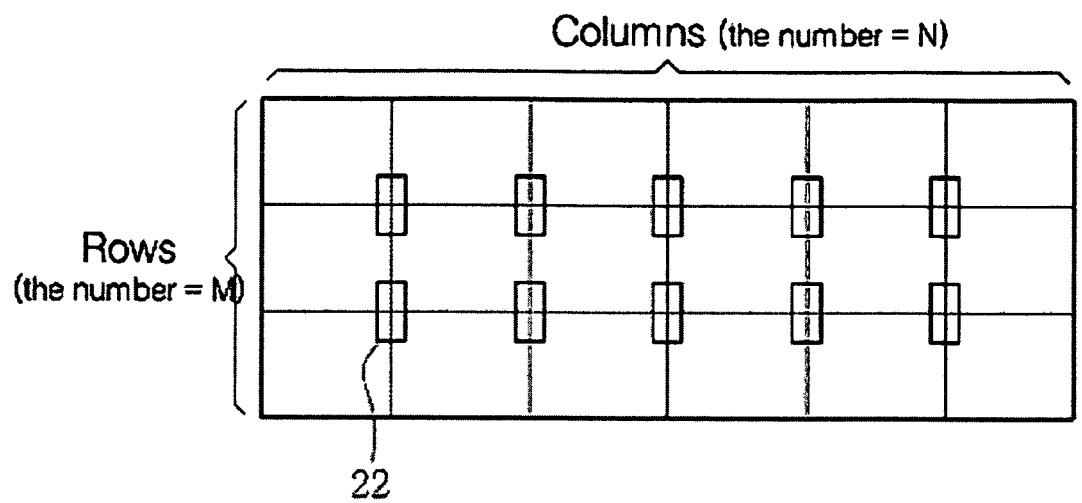
FIG. 6 is one embodiment of a pulse-sensing part array.

A pulse-sensing part 20 of the present invention, which uses the GMR device or the MTJ device as a unit cell, is arranged in an array type, as shown in FIG. 6.

Array types can be embodied variously depending on the objective of the pulse measurement and it is preferable that to get all pulse qualities by the traditional pulse diagnosis, the pulse-sensing part array is formed by dividing unit cells into three groups corresponding to "Chon", "Gwan", and "Cheok", arranging each group of unit cells as 2×5 or 3×6 matrix array and packaging.

And, the unit cell 22 of the pulse-sensing part 20 can be various in sizes depending on the process technology and the degree of the integration, and it is preferable that the size is about 1.0 mm×2.0 mm.

Figure 7:
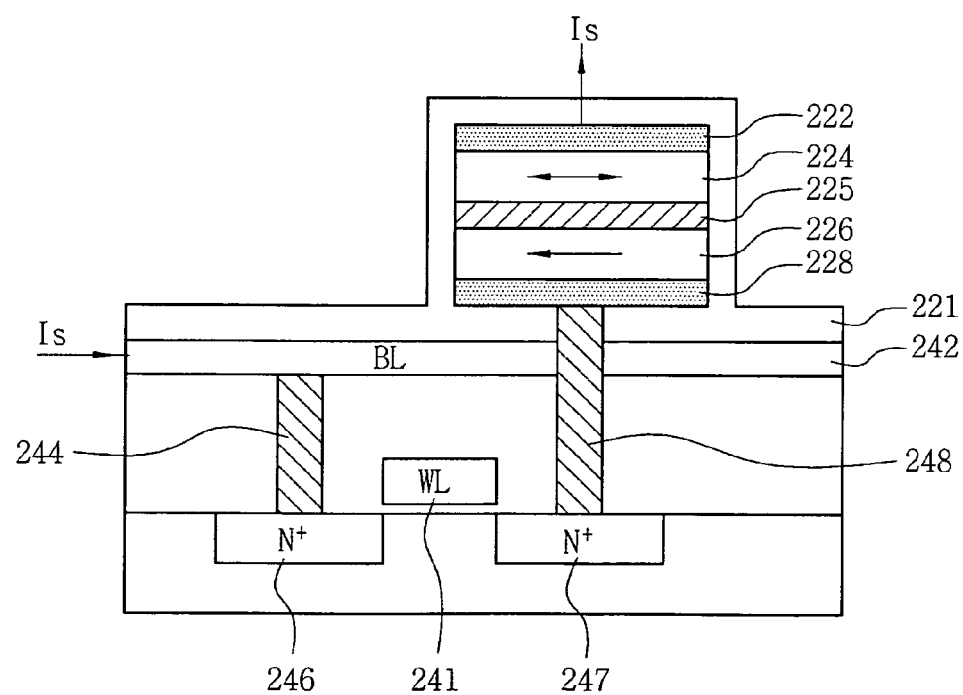
FIG. 7 is a cross-section of a unit cell of a pulse-sensing part array of the other embodiment.

In the other embodiment for an array type, pulse qualities of a desired measuring region can be obtained easily in short time by fabricating a switching device (for example, a NMOS device) and M×N matrix unit cells on one wafer, applying a sensing current $I_s$ to a bit line (BL, 242), as shown in FIG. 7 and controlling the sources of electricity of a word line (WL, 241) so that unit cells in the measuring region only can work. In FIG. 7, reference number 221 means a device protecting layer, 244 and 248 mean contacts for electrical connecting, and 246 and 247 mean a source or drain region of an NMOS device.

After all, the present invention is characterized by arranging minute unit cells 22 of the pulse-sensing part 20 appropriately, and therefore, it is not only possible to understand the time characteristics of the pulse by a pulse wave measurement, but also to understand fully the spatial characteristics of the pulse by a measurement of widths, lengths, degree of palpation of the pulse and so on.

In the last embodiment, it is preferable that a spatial part 30 is a constant pressure chamber, which maintains a predetermined pressure. In the present invention, a spatial part 30 functions to keep a predetermined space between the skin-contacting region 10 and the pulse-sensing part 20 and to transfer changes in the magnetic field by the magnetic material of the skin-contacting part 10 to the pulse-sensing part 20 as it is. Therefore, any means to keep a predetermined space and transfer changes in the magnetic field by the magnetic material of the skin-contacting part 10 to the pulse-sensing part 20 as it is, can be used in the present invention.

In the constant pressure chamber, a distance between the skin-contacting part and the pulse-sensing part can be determined based on the magnetic strength of the magnetic material of the skin-contacting part 10 and magnetic sensitivity of the unit cell 22 of the pulse-sensing part 20. If the magnetic material of the skin-contacting part 10 is a ribbon-type magnetic pad, of which magnetic strength is 200~300 Oe, it is preferable that the distance is maintained as 1~3 mm.

Furthermore, when a pressure controlling apparatus is adhered to the constant pressure chamber, it is possible to get easily pulse qualities at the state of "Bu", "Jung", and "Chim" of the traditional pulse diagnosis.

However, to show the function of the pressure controlling apparatus properly, it is necessary to embody the pulsimeter sensor according to the present invention into a wrist watch or a bracelet and transfer the increased pressure to the skin-contacting part 10 intact when pressure of the constant pressure chamber is increased.

In addition, a conventional pressure sensor can be adhered to the skin-contacting part 10, separately from the magnetic materials, and this can make up the functions that the pressure sensor have only.

So far, the preferable embodiments of the present invention has been described herein, however, it will be evident that the present invention cannot be defined only by the described embodiments herein and it will be understood that the invention herein described are generally applicable, and executed as various modified embodiments by those skilled in the art. For example, materials and numerical values for a skin-contacting part 10, a pulse-sensing part 20 and a spatial part 30 can be various within the technical thought of the present invention.

The present invention relates to a noninvasive medical pulsimeter sensor using magnetic thin films. By forming a pulse-sensing part array with magnetic sensors such as GMR devices, MTJ devices and the likes, over the skin-contacting part, which consists of a magnetic material, the present invention increases the integrity of sensors, minimizes the time for searching the pulse and it is applicable widely to a portable pulsimeter and the likes.

What is claimed is:

1. A pulsimeter sensor using magnetic thin films, including:
   a skin-contacting part formed with a magnetic material to be contacted to a skin to examine the pulse;
   a pulse-sensing part located some distance away from the skin-contacting part and formed as an array type of unit cells with two or more magnetic films; and
   a spatial part located between the skin-contacting part and the pulse-sensing part;
   wherein the unit cell of the pulse-sensing part array is a GMR (Giant Magneto Resistance) device; and wherein the pulse-sensing part array is formed by dividing thirty unit cells into three groups corresponding to "Chon", "Gwan" and "Cheok".

2. The pulsimeter sensor of claim 1,
wherein the magnetic material of the skin-contacting part is made of nano-magnetic particles of magnetic nano-bead type.

3. The pulsimeter sensor of claim 2,
wherein the nano-magnetic particles are one selected from Co, $Fe_3O_4$ and $Fe_2O_3$.

4. The pulsimeter sensor of claim 1,
wherein the magnetic material of the skin-contacting part is ultra thin.

5. The pulsimeter sensor of claim 4,
wherein the ultra thin magnetic material of the skin-contacting part is a ribbon-type magnetic pad.

6. The pulsimeter sensor of claim 5,
wherein the ribbon-type magnetic pad of the skin-contacting part is made of plastic magnets, of which the strength of the magnetic field is 200~300 Oe at a 3 mm distance.

7. The pulsimeter sensor of claim 1,
wherein the GMR device is comprised of a lower layer, a middle layer and an upper layer,
wherein the lower layer, facing the skin-contacting part, is a free (variable ferromagnetic) layer,
wherein the upper layer is a pinned (fixed ferromagnetic) layer, and
wherein the middle layer is a Cu layer as a nonmagnetic layer.

8. The pulsimeter sensor of claim 7,
wherein the free layer and the pinned layer are comprised of two or more thin films, which are different from each other, respectively.

9. The pulsimeter sensor of claim 8,
wherein the free layer is formed of a CoFe layer and a NiFe layer orderly from one side of the nonmagnetic layer, and
the pinned layer is formed of a CoFe layer and a IrMn layer orderly from the other side of the nonmagnetic layer.

10. The pulsimeter sensor of claim 9,
wherein the Cu layer is 2.5~2.7 nm thick, the CoFe layer of the free layer is 1.8~2.2 nm thick, the NiFe layer is 3.8~4.2 nm thick, the CoFe layer of the pinned layer is 3.3~3.7 nm thick, and the IrMn layer is 13.0~17.0 nm thick.

11. The pulsimeter sensor of claim 1,
wherein the unit cell of the pulse-sensing part is about 1.0 mm×2.0 mm, and the array is arranged as a package of the unit cells with 2×5 matrix structure at each "Chon", "Gwan" and "Cheok".

12. The pulsimeter sensor of claim 1,
wherein the array of the pulse-sensing part is made by fabricating switching devices and M×N matrix unit cells on one wafer, cutting the M×N matrix unit cells into specific size and forming them as one package.

13. The pulsimeter sensor of claim 1,
wherein the spatial part is a constant pressure chamber, which maintains a predetermined pressure.

14. The pulsimeter sensor of claim 13,
wherein in the constant pressure chamber, a distance between the skin-contacting part and the pulse-sensing part is maintained as 1~3 mm.

15. The pulsimeter sensor of claim 14,
wherein to the constant pressure chamber, a pressure controlling apparatus is adhered.

16. The pulsimeter sensor of claim 15,
wherein to the skin-contacting part, a pressure sensor is adhered separately from the magnetic materials.

* * * * *